United States Patent [19]

Sanderson et al.

[11] 4,349,118
[45] Sep. 14, 1982

[54] STERILIZING AND STORING MEDICAL ITEMS

[75] Inventors: Roger S. Sanderson, 24772 Santa Clara, Dana Point, Calif. 92629; Robert C. Whelchel, Newport Beach, Calif.

[73] Assignee: Roger S. Sanderson, Dana Point, Calif.

[21] Appl. No.: 144,068

[22] Filed: Apr. 28, 1980

Related U.S. Application Data

[63] Continuation of Ser. No. 923,359, Jul. 10, 1978, abandoned, which is a continuation of Ser. No. 734,228, Oct. 20, 1976, abandoned, which is a continuation-in-part of Ser. No. 703,044, Jul. 6, 1976, Pat. No. 4,196,166, which is a continuation-in-part of Ser. No. 640,824, Dec. 15, 1975, abandoned.

[51] Int. Cl.³ .................. A61L 2/06; B65D 81/20
[52] U.S. Cl. ............................ 220/201; 422/26; 220/DIG. 19
[58] Field of Search .............. 220/201, 203, 208, 209, 220/304, 363, 366, 87, DIG. 19; 422/25-27, 40, 107, 112, 293, 296

[56] References Cited

U.S. PATENT DOCUMENTS

| | | | |
|---|---|---|---|
| 1,183,815 | 5/1916 | Hasty | 137/72 |
| 2,008,835 | 7/1935 | Rawcliffe | 137/468 |
| 2,092,445 | 9/1937 | Doulgheridis | 118/121 |
| 2,097,585 | 11/1937 | Carson | 236/92 H |
| 2,455,305 | 11/1948 | Heva | 137/468 |
| 2,591,767 | 4/1952 | Andres | 220/203 |
| 2,698,022 | 12/1954 | Fanoe | 137/468 |
| 2,715,251 | 8/1955 | Vischer | 422/26 |
| 2,742,927 | 4/1956 | Frumet, Jr. | 137/468 |
| 2,997,397 | 8/1961 | Doulgheridis | 215/355 |
| 3,061,196 | 10/1962 | Bauerlein | 251/144 |
| 3,468,471 | 9/1969 | Linder | 229/62.5 |
| 3,561,918 | 2/1971 | Ray | 206/363 |
| 3,621,951 | 11/1971 | Schmid | 137/468 |

FOREIGN PATENT DOCUMENTS 1642161 8/1970 Fed. Rep. of Germany .
1074275 7/1967 United Kingdom .

Primary Examiner—Joseph Man-Fu Moy
Attorney, Agent, or Firm—Knobbe, Martens, Olson, Hubbard and Bear

[57] ABSTRACT

A sealed container provides with a plug valve which employs a heat responsive band having one end attached to the side of the plug which is on the outer side of the plug when the plug is positioned in the container wall. The other end of the band extends around the edge of the plug holding the edge away from a valve opening in the wall of the container. This inner end of the band is connected through a wire to a fusable pin centrally positioned on the inner side of the plug. At the desired time, the fuse melts releasing the wire and the ban shrinks or retracks, releasing the edge of the valve member allowing it to seal against the container wall.

3 Claims, 13 Drawing Figures

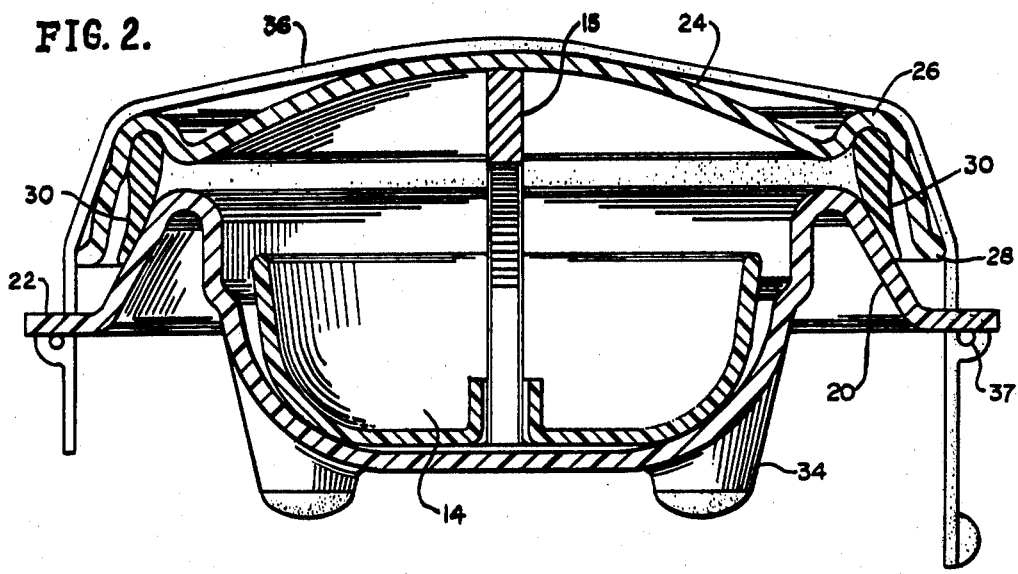
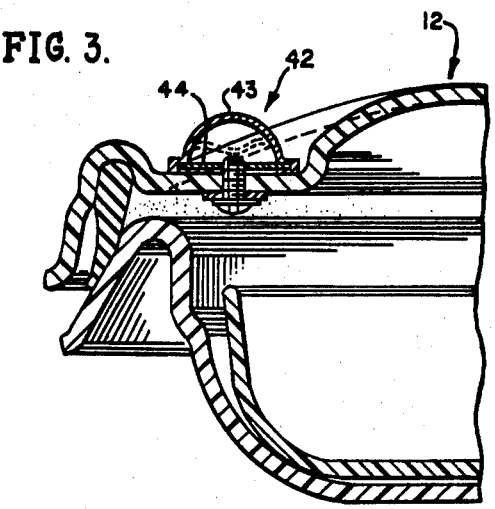
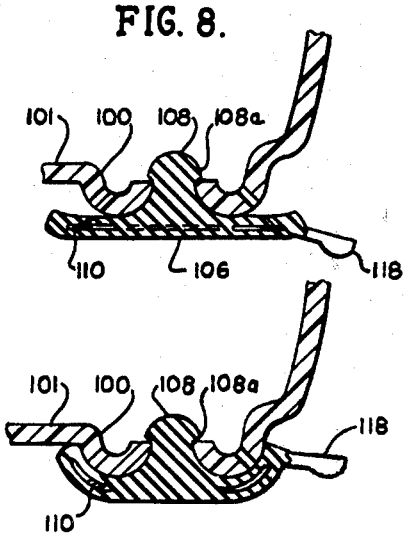
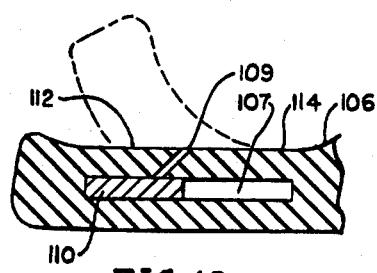

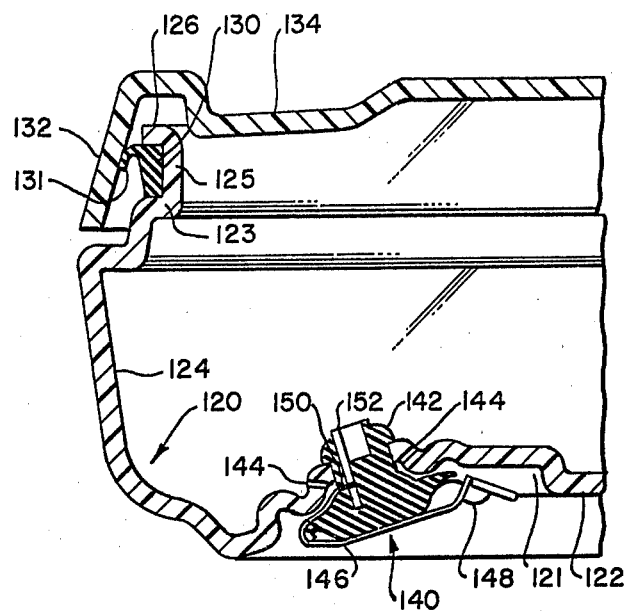
FIG. 11.
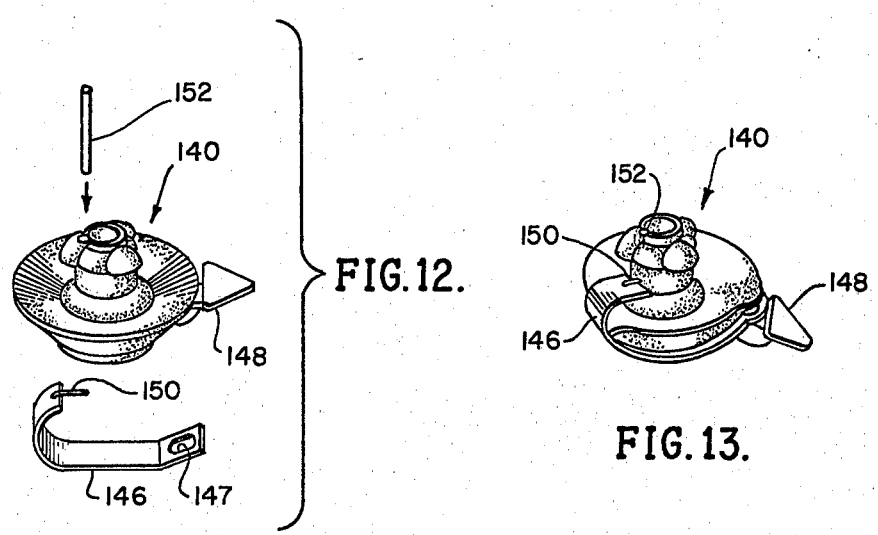
FIG. 12.
FIG. 13.

STERILIZING AND STORING MEDICAL ITEMS

CROSS REFERENCE TO RELATED APPLICATIONS

This invention is a continuation of U.S. patent application Ser. No. 923,359, filed July 10, 1978, now abandoned which is a continuation of U.S. Ser. No. 734,228, filed Oct. 20, 1976, abandoned which is a continuation-in-part of U.S. Ser. No. 703,044, filed July 6, 1976 now U.S. Pat. No. 4,196,166, which is a continuation-in-part of application Ser. No. 640,824, filed Dec. 15, 1975 entitled STERILIZED STORAGE CONTAINER (now abandoned).

An alternate approach includes a disposable, resilient valve member which plugs into a hole in the wall of the container and covers a valve orifice into the container. A washer-like fuse element fits into the valve member to bias it into an open position. When the fuse melts after sterilization, the valve member will snap into closed position.

Another variation of a plug valve employs a heat responsive band having one end attached to the side of the plug which is on the outer side of the plug when the plug is positioned in the container wall. The other end of the band extends around the edge of the plug holding the edge away from a valve opening in the wall of the container. This inner end of the band is connected through a wire to a fusable pin centrally positioned on the inner side of the plug. At the desired time, the fuse melts releasing the wire and the band shrinks or retracts, releasing the edge of the valve member allowing it to seal against the container wall.

This invention relates to an improved apparatus for storing sterile items while they are being sterilized, while they are being stored awaiting use, while they are in the process of being used, and after they have been used and are awaiting resterilization.

The most commonly used method for sterilizing surgical instruments and other medical items is to place them in towels which are enclosed in a sheet and taped shut for placement in a sterilizing autoclave. Sterilizing steam applied to the interior of the autoclave penetrates the porus material surrounding the items to be sterilized. The moisture is removed by a drying cycle within the autoclave. The sterile package is then either used immediately or placed in storage for future use. If the pack has not been used in a period of time, typically twenty days, it must be returned to the autoclave for resterilization. It is estimated that two-thirds of sterilization work load in many hospitals is for items that were not used within the shelf life of the pack. This of course is an expensive and inefficient procedure.

Another shortcoming of the towel arrangement is that, unless adequate labeling is used, the contents within the towel are unknown. Once the package is opened to check the contents, the sterilization is, of course, lost unless the contents are immediately used. If the contents are not what the user desires, then the sterilization of that particular package must be repeated.

Thus, a need exists for a practical and reliable system for handling sterile items and for maintaining sterility. A container surrounding the items to be sterilized could be completely sealed before being placed in the autoclave, but the contents are then not subjected to a sterilizing steam. Instead, the atmosphere within the sealed container would be closer to dry heat sterilization which requires higher temperatures and longer periods of time than does moist heat. Also, an autoclave typically has significant pressure variations as a result of vacuum phases exhausting air and steam, and a pressure phase applying steam. Thus a sealed container would have these pressure variations applied to its exterior which might cause breakage or damage to the container.

In the earlier of the above-referenced patent applications, a system is disclosed wherein a container is placed within an autoclave with its lid slightly open, and means are provided for automatically closing the lid at a predetermined time near the end of the sterilizing cycle. While this system is highly desirable, moving the entire lid at the desired time introduces certain complexities.

SUMMARY OF THE INVENTION

The present invention includes a closed container for holding the items to be sterilized and stored, and a novel valve means which is open during sterilization and then automatically closes at a desired point. The valve is a resilient flexible member having a surface shaped to conform to the container wall around an opening in the wall, and having means for mounting the valve member on the container covering the valve opening. Temperature responsive means holds the valve member in an open position, unnatural to its resilient tendency to close. The temperature responsive means includes a holding element which is connected between two points on the valve member holding the valve member in a valve-open, distorted configuration, the element being under tension due to the resiliency of the valve member. The temperature responsive means releases the valve member at a predetermined temperature allowing the resilience of the valve member to close the valve opening.

For a more thorough understanding of the invention, refer to the following detailed description and drawings in which:

FIG. 2 is a cross-sectional view of the container;

FIG. 3 is a cross-sectional view on line 3—3 of FIG. 1, illustrating a vacuum indicator;

FIG. 8 is a cross-sectional view of a second embodiment of a valve member for the container of FIG. 1, the valve being shown in open position;

FIG. 9 is a cross-sectional view of the valve of FIG. 8 with the valve in closed position;

FIG. 10 is an enlarged fragmentary view showing a portion of the valve of FIG. 8 in the open position with solid lines, and in closed position in dotted lines;

FIG. 11 is a side elevational view of another form of resilient valve member which plugs into a wall of a container which has a cylindrical shape and also has another form of gasket;

FIG. 12 is an exploded perspective view of the valve of FIG. 11; and

FIG. 13 is a perspective view of the valve member of FIG. 11 in cocked position ready to be mounted on the container.

Figure 1:
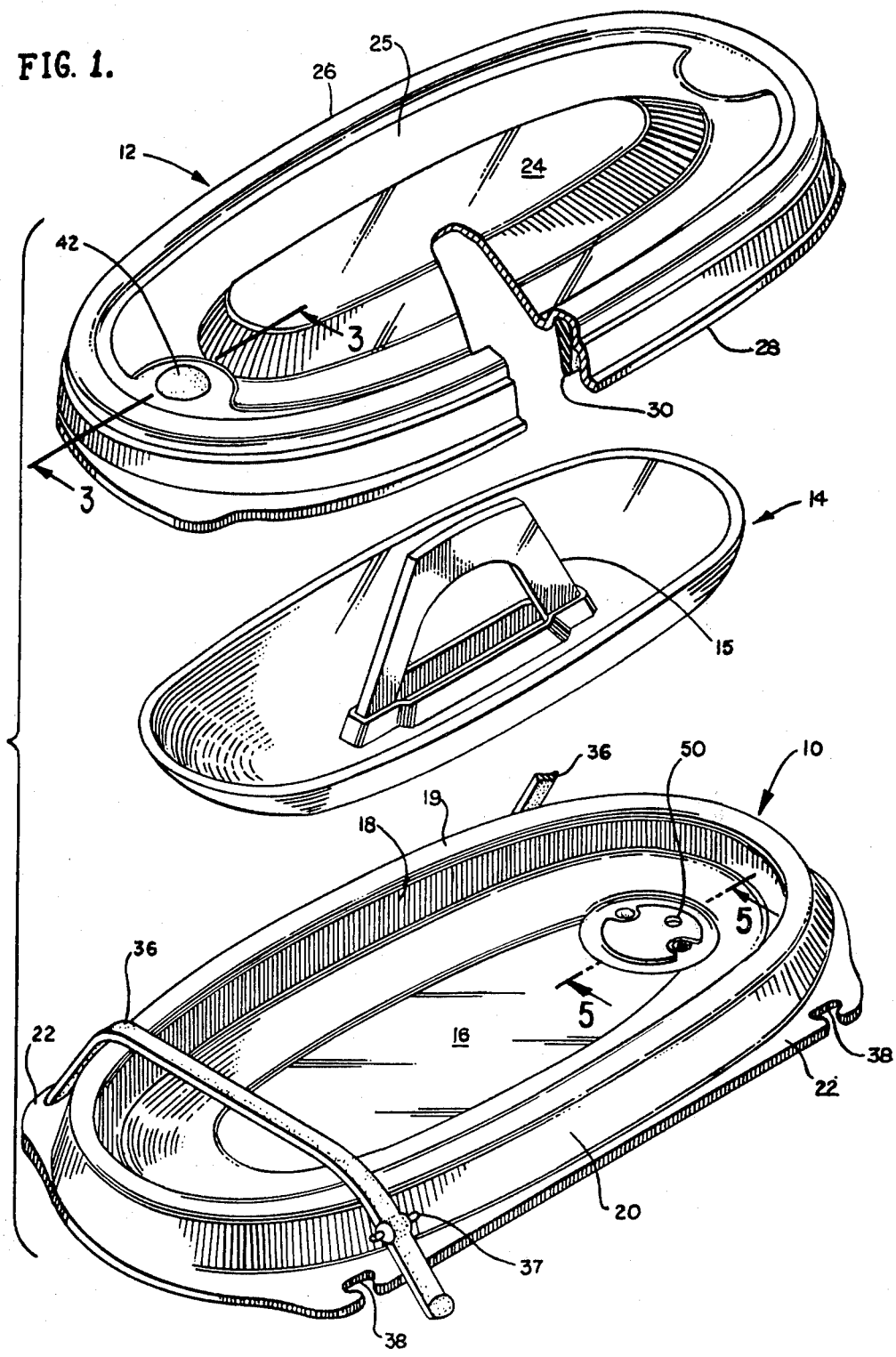
FIG. 1 is an exploded perspective view of the container of the invention showing the lid, and internal tray and the base.

Referring now to the drawings, the container shown in FIG. 1 includes a base 10, a cover or lid 12 and an internal support or tray 14. As can be seen, the container is elongated and relatively flat having rounded corners so as to provide a somewhat racetrack configuration. The base has a bottom wall 16 and a side wall 18 which terminates with a rounded upper edge 19 and a downwardly sloping flange 20, and a further horizontally extending flange portion 22. The lid 12 has a top wall with a central flat section 24 and a rounded, downwardly sloping section 25, and a surrounding edge portion 26 which slopes upwardly, horizontally, and then downwardly and outwardly to form a shape which fits over the upper edge 19 of the base 10. The lid further includes a short outwardly extending peripheral flange 28.

A large flexible gasket 30, shown more clearly in FIG. 2 is attached to the lid 26 and includes a downwardly extending flexible portion which resiliently engages the downwardly and outwardly flaring wall 20 of the base. With the lid pressed tightly onto the base, a seal is formed where the lower edge of the gasket 30 engages the wall 20 as illustrated in FIG. 2. Also, the upper end of the gasket fits snuggly within the lid to form a seal in that area. As also seen from FIG. 2, the base has a plurality of legs 34 supporting the bottom wall of the base slightly from the supporting surface.

The container is further provided with a pair of flexible retaining straps 36, one on each end of the container. The strap 36 has a retaining pin 37 on each end to fit within a slot 38 formed in the flange 22, and holds the end of the strap in that position. The strap extends over the lid to positively hold it into position, and to maintain the container sealed after it is sterilized.

The tray 14 has a configuration which conforms to the interior of the base 10, and has an upwardly extending handle 40 dimensioned and shaped to engage the inner surface of the lid 12 when the lid is tightly sealed on the base. The handle provides additional support to the cover in the event a strong vacuum exists within the container.

A vacuum indicating unit 42 is mounted in one end of the cover 12. The unit 42 includes an upper resilient member 43 which is held in sealed position against the cover by a plate 44 which fits within a recess in the flexible member 43. The plate is urged in a direction towards the cover by means of a screw threaded through the cover from its lower side. The screw 46 has an internal passage therethrough so that the interior of the valve member 43 is exposed to the pressure within the container.

Figure 5:
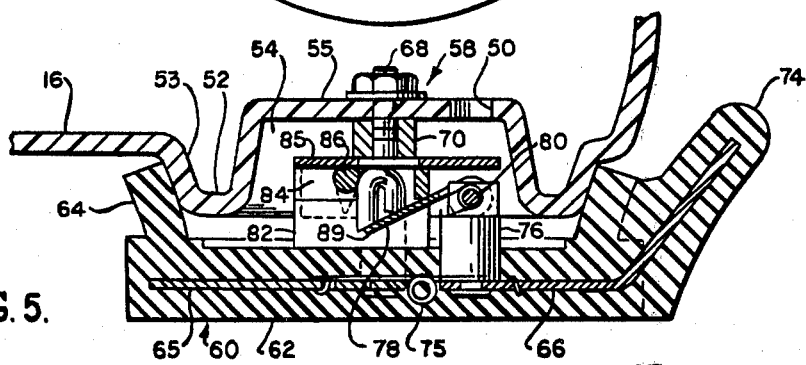
FIG. 5 is a cross-sectional view of the valve of FIG. 4 showing the valve in closed position.

As shown in FIG. 1, one or more valve openings 50 are formed in the lower wall 16 of the base 10. Referring now to FIG. 5, it may be seen that the lower wall of the container is formed with an annular outwardly extending protuberance 52 having an outwardly facing surface 53. The wall then extends inwardly slightly, thus creating a shallow, circular recess or cavity 54 and a circular wall section 55.

A valve assembly 58 is attached to the circular wall section 55 by suitable fastening means. The valve assembly 58 includes a valve member 60 made of rubber-like material and having a flat circular bottom 62 and an upwardly extending annular side wall 64 having an inner surface which resiliently engages the outwardly extending wall surface 53 to seal access from the container exterior into the interior by way of the valve opening 50. A pair of stiffner plates 65 and 66 are embedded in the bottom wall 62 of the valve member 60 to provide some rigidity to the bottom wall. A pair of mounting screws or pins 68 are attached to the plate 65, and extend through support tubes 70, through holes in the wall 55 and are secured to the wall 55 by suitable nuts 72 threaded onto the end of the screws 68. The nature of the connection is such that the annular wall 64 of the valve member 60 is biased into sealing engagement with the wall surface 53 in a normally closed position.

Figure 6:
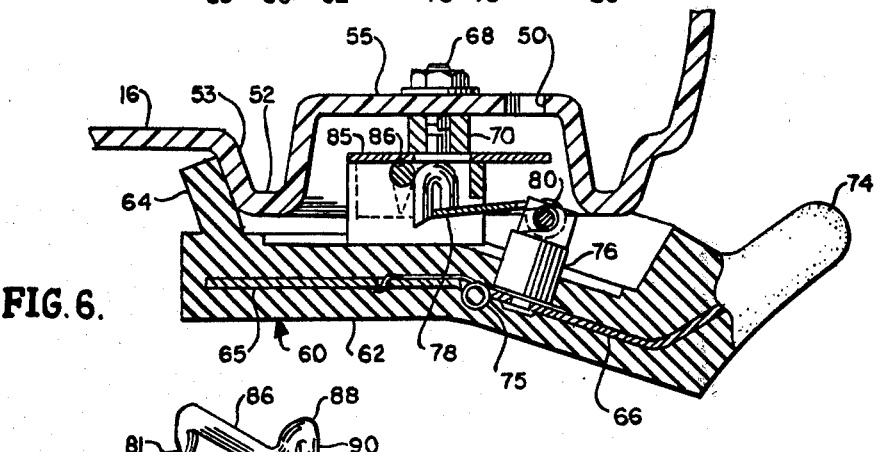
FIG. 6 is a cross-sectional view of the valve showing the valve in open position.
Figure 7:
FIG. 7 is a perspective view of a member used in holding the valve open.

One edge of the valve member 60 is formed with an upperwardly and outwardly extending portion which forms a manually operable valve opening lever 74. An extension of the plate 66 is embedded in the lever portion 74 so that when the lever 74 is manually depressed, the valve member may be moved into an open position as shown in FIG. 6. As stated, the resiliency of the valve member 60 is such that it normally wants to assume the position shown in FIG. 5. If desired, suitable spring means may also be employed to further urge the valve member into closed position. As one arrangement, a coil spring 75, FIG. 4, may be positioned in the uppersurface of the wall 60 of the valve member with one end of the coil engaging the plate 65 and the other end engaging the plate 66 in a manner to provide a force which biases the valve member into its closed position.

Figure 4:
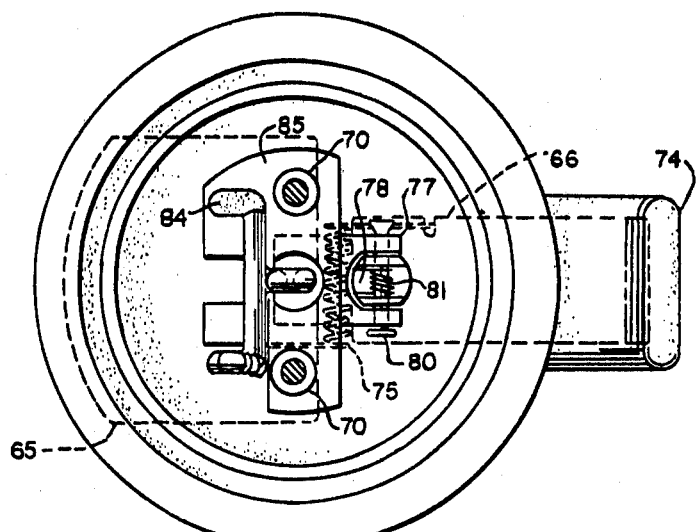
FIG. 4 is a plan view of the container valve.

To hold the valve in the open position, there is provided a holding or cocking means which includes a support member 76 suitably attached to the plate 66 and the bottom wall 62 of the valve member 60. The support member has a pair of upwardly extending arms 77 as shown in FIG. 4. A latching lever 78 is pivotally mounted to a pin 80 supported by the arms 77 of the support 76. Urging the latching lever 78 into a clockwise direction as viewed in FIGS. 5 and 6 is a suitable spring 81 positioned on the pin 80.

A small housing 82 is attached to the other half of the valve member 60 and the plate 65 by means of the mounting screws 68. The support housing includes a shallow compartment 83 filled with a metal fuse 84 which will melt at a desired temperature. The metal is sealed within the housing by a cover plate 85 also held in place by the mounting screws 68. An irregular shaped latch 86 is pivotally mounted on the housing 82 with one end of the latch 86 being journaled adjacent the metal fuse 84, and a tang 87 on the latch 86 is positioned within the fuse metal 84. A spring 91 has one end attached to the latch 86, while the opposite end of the spring is anchored beneath one of the support posts 70. The spring 91 urges the latch 86 into a counter clockwise direction as viewed in FIG. 5.

Rigidly attached to the latch 86 is a small somewhat U-shaped portion 88 having a latching leg 89 and a shorter cam leg 90 both of which cooperate with the end of the latch lever 78 in holding the valve member in the open position and releasing it from the open position.

Turning now to the operation of the embodiment of FIGS. 1–7, assume the container is empty and that the cover or lid 12 is separate from the base 10. The items to be stored are placed within the container and the cover is placed into position on the base. The cover is held in this position by extending the straps 36 over the top of the cover and hooking the ends of the straps into the notches 38 formed in the base. Assume that the valve member 60 is in the open position of FIG. 6 and that the fuse metal 84 is solid. In this condition, the valve member 60 is held open position by virtue of the fact that the end of the latch lever 78 engages the side of the latch leg 89 as shown in FIG. 6.

The container is then placed within an autoclave or other sterilizing apparatus. If an autoclave is used, one or two vacuum phases are applied to the interior of the autoclave to draw contaminated air from the container. Since the valve is open, the air within the container is drawn out of the hole 50 in the bottom wall section 55. When steam or other sterilizing fluid is applied to the exterior of the container, it can flow freely into the interior of the container through the opening 50. The high temperatures associated with the sterilizing operation will melt the fuse metal 84 after a predetermined time which is selected to be some time after the container and its contents have been sterilized. Preferably, this would be towards the end of the heating cycle and before the final vacuum cycle as typically applied in an autoclave to remove the steam from the autoclave. When the fuse metal 84 melts, the resiliency of the valve member 60 plus the urging of the spring 75 will move against the latching leg 89 pivoting the member 86 against the urging of the weaker spring 91. The tang 81 is permitted to move within the fuse metal since the metal is no longer rigid. As the U-shaped member 88 pivots with the member 86, the cam leg 90 engages the upper surface of the latch lever 78 camming it downwardly against the biasing of the spring 81 until the tip of the lever 78 slips past the lower edge of the leg 89. Once this occurs, the valve member quickly moves to the position shown in FIG. 5 wherein the flexible wall 64 of the valve member is once more sealed against the wall surface 53. The latch lever 78 is depressed beneath the end of the latch leg 89. Note that the spring 91 urges the member 86 into the position shown wherein the end of the lever 78 is engaged on the end of the leg 89. Note also that the end of the leg 89 is beveled at the approximate angle of the orientation of the lever 78 in the valve closed position.

The container is now sealed with its cntents sterilized so that the container can be removed from the sterilized atmosphere. However, if the unit is sterilized within an autoclave, there will usually be a further vacuum phase after the valve is closed. If the autoclave pressure surrounding the container becomes significantly greater than the pressure within the container the atmosphere within the container can leak from the container, past the flexible gasket 30. This is due to the configuration of the flange surface 20 on the base 10 and due to the size and flexibility of the lower end of the gasket. Since the relationship between the flexible wall 64 and the surface 53 is somewhat similar, it is possible that some pressure relief may occur at that area too. This leakage is deirable in that there may be some residual steam within the container and it is preferable that the container be relatively dry.

With a strong vacuum applied to the exterior of the container, a vacuum will be created on the interior. Thus, once the pressure is brought back to atmospheric, a vacuum will exist within the container; and neither the gasket nor the valve will permit leakage into the container. The curved configuration of the container is such that its walls can withstand a relatively high pressure differential between the interior and exterior of the container. However, as a precautionary measure with larger size containers, it may be desirable to have the handle 40 of the tray 14 engage the interior upper surface of the lid as shown in FIG. 2 to provide additional strength.

The container with its contents may now be moved to whereever desired such as to storage for future use or it may be carried directly to where its contents are to be used. When the container is to be opened, it is first necessary to relieve any vacuum that may exist. To do this, it is only necessary to depress the valve lever 74 moving the valve into the open position. The sound accompanying the vacuum relief will indicate that the contents of the container are still sterilized. Conversely, if leakage has occurred, the absence of the sound will warn the individual opening the container that the contents may no longer be sterile. The flexible member 43 of the indicator 42 will also tell the condition, by being depressed when there is vacuum and raised when there is no vacuum.

Due to the excellent nature of the seal provided by the gasket 30, it is quite likely that even though air molecules may, after a long period of time, seep into the container past the gasket, most microrganisms are much larger and cannot necessarily pass the seal. Thus, to that extent, the gasket serves as a filter even if the vacuum is ultimately lost.

Shortly after the sterilizing temperatures begin to fall, the fuse metal will once more solidify, holding the latch leg 89 in the position shown in FIG. 6. Thus, when the valve is open, the tip of the latch lever 78 will slide off the end of the latch leg 89 and be urged slightly in a clockwise direction by its coil spring 81 into engagement with the return leg 90. When the lever 74 is released, the end of the latch lever 78 once more engages the side of the latch leg 89 holding the valve in its open position. Thus, depressing the lever 74 not only relieves the vacuum within the container but simultaneously cocks the valve member in an open position so that the container is once more ready to be sterilized. This feature is very important in that it is not necessary for a person to remember to open the valve before placing the container back into the sterilizing apparatus. Thus, if the container has been used to sterilize surgical instruments for example, and the container is taken directly into the operating room, the instrument can be removed directly from the container, used, washed if necessary, and then returned to the container for resterilization.

If it is preferred that the container not be taken directly into the operating room, the container may be opened just outside the operating room and only the sterile tray and the instruments on the tray be carried into the operating room. Again, after the instruments are used, they can be returned to the tray and the tray returned to the container for resterilization. It is only necessary that the cover be once more strapped into position and the container can then be placed within the autoclave for sterilizing.

As a further variation of this procedure, the container may be placed within a sterilizing bag (not shown) during the sterilizing cycle. There is a bag available on the market, sold by C. K. Bord Inc. and described in U.S. Pat. No. 3,595,465 into which the container could be placed and inserted into the autoclave. The bag is such that is will permit steam to penetrate it during the sterilizing cycle but will be sealed to a considerable extent during the sterilizing cycle. With this situation, the container would be removed from the bag just prior to be taken into the operating room. Thus, the entire container would still be reasonably sterile and the instruments could be taken directly from the base of the container. The upper edge of the base would still be sterile in the event a person's hand should touch that area in removing instruments.

One of the advantages of the arrangement described above is that the valve as well as the container is reuseable. However, as another approach, there is illustrated in FIGS. 8-10 a second embodiment of the invention comprising a disposable, simplified valve still using the fuse principle. As seen in FIG. 8, a small annular protuberance 100 is formed in the wall 101 of a container similar to that shown in FIG. 1. One or more holes 102 are formed in the annular wall 100 to permit access to the container. An additional hole is formed in the middle of the annular wall 100 to receive a disposable valve member 106 provided to control access to the container through the holes 102. More specifically, the valve member 106 includes an integral, inwardly extending projection 108 which is rounded and sized so that it can be pushed into the hole in the center of the annular wall 100 as shown in FIG. 8. A peripheral shoulder 108a engages the interior wall of the container to hold the valve in position on the container.

The valve member 106 is formed of a resilient rubber-like material which permits the projection 108 to be forced into the hole in the container wall. The member 106 is molded in the configuration shown in FIG. 9 which comprises a circular shape with the periphery of the member curving upwardly into a saucer configuration tightly engaging the outer surface of the annular wall 100 and enclosing the valve openings 102 into the container. Thus, in the condition shown in FIG. 9, the valve is closed which might be thought of as its normal condition in that that is the position the rubber valve member 106 wants to assume. Note also that if a vacuum exists within the container, the vacuum helps hold the valve member tightly against the holes 102.

To hold the valve in its open position, there is provided a fuse 110 in the form of a ring having a flat, washer shaped configuration. As seen in FIG. 10, the valve member 106 is formed with an internal slot 107 with a smaller diagonal slit 109 forming two resilient flaps 112 and 114. After the valve member is molded into the configuration shown in FIG. 9, the fuse element is inserted into the slot within the valve member by depressing the periphery of the valve member so that the fuse washer may be inserted into the slot 107 through the slit 109. Note that the fuse occupies only the outer portion of the slot 107. With the fuse so positioned, the configuration of the valve member is as shown in FIG. 8 wherein the outer periphery of the outer valve member is held away from the openings 102. The valves would normally be furnished in this condition. Thus, a user of the container can simply take a valve of this type and snap it into the container in the position shown in FIG. 8. The container is then ready to be sterilized.

At the appropriate time in a heat sterilizing cycle, the fuse washer will melt, allowing the valve member to assume its normal molded position, as indicated by the broken lines in FIG. 10. Thus, the valve is closed as shown in FIG. 9. The closing movement of the valve member together with gravity causes the melted fuse metal to flow to the inner end of the slot 107 within the valve member as shown in FIG. 9. Thus, when the fuse metal once more solidifies, it will not interfere with the sealing operation of the valve. Instead, it will tend to hole the valve in the closed position to some extent.

When it is desirable to release the vacuum within the container, an integral tab 118 formed on one edge of the valve member is pulled away from the container thus allowing the vacuum to be relieved through the adjacent hole 102. The container lid can then be moved. The valve member 106 can also be removed by simply pulling harder on the valve tab. When the container is to be resterilized, a new valve member can be quickly snapped into position. A new valve member can, of course, be installed as soon as the old one is removed.

Referring now to FIG. 11, a generally cylindrical container is shown having a base 120 with a bottom wall 122 and an upwardly extending side wall 124. The upper portion of the side wall includes an inwardly extending shoulder 123, a recessed cylindrical portion 125, and an outwardly extending flange 126 on the upper edge of the wall portion 125.

A resilient gasket 130 is positioned beneath the flange 126 and is dimensioned to tightly engage the cylindrical wall portion 125. The gasket further includes an outwardly and downwardly extending flexible flange 131, which engages the inner surface of a downwardly and outwardly extending side wall 132 on a cover 134 for the container. Like the gasket 30 in FIG. 2, the gasket 130 not only seals the cover to the base, but also acts as a one-way valve to permit gas to be withdrawn from the container but will prevent gaseous flow into the container.

The bottom wall 122 of the container is dished upwardly, and a recess 121 is formed to one side of the bottom wall. A valve member 140 molded of resilient rubber-like material is positioned in the recess 121. The valve member is similar to the member 106 of FIG. 9 and includes an inwardly extending projection 142 which is rounded in size so that it can be pushed into a hole in the bottom wall 122. The valve member is molded in the configuration shown in FIG. 12, which comprises a normally circular shape with the periphery of the member curving upwardly into a saucer-like configuration to engage tightly the outer convex surface of the surrounding wall, and thus close the valve openings 144 leading into the container.

To hold the valve member open, there is provided a band 146 made of a well-known plastic, heat shrinkable material which will shrink when heated to certain temperature and then cooled. One end of the band has an opening 147 which fits over an arrowhead-shaped end on a tab 148 formed integral with the valve member. As seen from FIG. 11, the band extends around a portion of the edge of the valve member 140 and holds that edge portion downwardly and away from the bottom wall 122 so that the openings 144 in the container are not sealed. The inner end of the band 146 has one end of a metal element or wire 150 attached to it, and the other end of the wire extends into the central core of the valve member where it is attached to a fuse 152 positioned within the central core or projection 142. The fuse pin 152 is made of metal which will melt at a desired temperature, specifically after it has been exposed a predetermined time to autoclave sterilizing temperatures. As indicated above, this would be towards the end of the heating cycle and before the final vacuum cycle as typically applied in an autoclave to remove the steam from the autoclave.

In use, the valve member may be furnished in the form shown in FIG. 13, cocked and ready to be inserted into the container in the position shown in FIG. 11. Preferably, however, the valve member is furnished with the wire 150 attached to the fuse pin 152 and to the band 146. When the device is to be used, it is cocked by hooking the band to the tab 148 by slipping the hole 147 over the tab.

With the valve member positioned as shown in FIG. 11, the container is ready for use in a sterilizing operation. The container, along with its contents are positioned in an autoclave or other sterilizing environment with the cover 134 in closed position. When steam enters the autoclave, it can flow freely into the container through the openings 144 in the bottom wall. After the desired sterilizing temperatures have been reached, the fuse metal will melt releasing the wire 150. The resiliency of the valve member helps withdraw the wire from the core of the valve member; also, the heat causes the band 146 to shrink or retract so that the wire 150 once released from the fuse metal, is quickly withdrawn around the edge of the valve member. Thus, the valve member is free to seal against the annular surface on the bottom wall surrounding the valve openings 144, thus blocking fluid flow into the container through these openings.

At the end of the sterilizing cycle, the container cools and the fuse metal captured in the plug solidifies, and the interior of the container is sealed in sterilized condition. If a vacuum is applied to the container exterior, air pressure in the container can be released between the gasket flange 131 and the cover wall 132. Reverse flow into the container after the vacuum is withdrawn is prevented, however, because pressure on the exterior of the container holds the gasket flange 131 sealed against the wall 132. The band 148 can now be removed from the tab 148 if desired.

When it is desired to open the container, the vacuum in the container can be relieved by pulling on the tab 148 so that the adjacent edge of the valve member 140 is withdrawn from the container wall permitting air to enter the container. If desired, a filter (not shown) may be positioned over the opening 144 and the projection 142 to filter the incoming air.

A stronger pull on the tab will withdraw the plug valve member completely from the container wall. When the container is to be reused, it is only necessary to insert a new valve member in the cocked position as shown in FIG. 13 so that the container is ready to be reused in a sterilizing cycle.

One of the advantages of this form of the invention is that the valve can be returned to a service center for recycling or recocking. In doing this, the old fuse metal is withdrawn and a new wire 150 previously attached to a new fuse pin is inserted into the open end of the projection 142 and out through the side of the projection, with the new pin being positioned in the projection as shown in FIG. 11. The other end of the wire is then attached to a new band 146; and the band is then ready to be attached to the tab, either at the service center or by the user.

One of the features of the container is the self-leveling characteristic of the cover 134 with respect to the base 120. That is, the cover need not be perfectly positioned on the base when the container is placed in an autoclave. The flange formed on the upper end of the sidewall 124 limits the downward movement of the cover in any particular area. During the last vacuum phase of an autoclave cycle, air and moisture within the container is drawn out of the container past the gasket flange 131 as explained above. When atmospheric pressure is introduced to the autoclave, the gasket flange 131, as well as the valve member 140 prevents air flow into the container. Thus, the pressure differential between the interior and the exterior of the container forces the cover 134 more tightly onto the container base 120. During this action, the flange on the upper end of the sidewall 124 limits cocking movement of the cover so that the cover is essentially self-leveling.

What is claimed is:

1. Apparatus for containing items while being sterilized or stored comprising:
   means forming a container including a plurality of walls with an opening in one of the container walls;
   a resilient, flexible valve member for controlling fluid flow through said opening, said member having a surface shaped to conform to the container wall around said opening, and having means for mounting said member on the container in a manner to cause said surface to engage the container thereby covering said opening;
   temperature responsive means holding said valve member in an open position unnatural to the resilient tendency of the valve member wherein said opening is not covered by the valve member, said temperature responsive means including an element having first means attached to said valve member at one point on the exterior of said valve member and second means connected to the valve member at a second point on the exterior of the valve member spaced from said one point, the distance between said points as measured along the surface of the valve member being greater than the distance between said first and second means on said element as measured by a straight line connecting said first and second means so that said element is held in tension between said points due to the resiliency of said member and said resilient valve member is distorted into and held by said element in a configuration wherein an edge of said valve member is held in said open position, said temperature responsive means being responsive to a predetermined temperature to release said edge and allow the resilience of the valve member to move said edge to a closed position.

2. The apparatus of claim 1 wherein said temperature responsive means includes material which will weaken at said temperature to release the valve member from being held in said open position, thus allowing the valve member to move to said closed position.

3. The apparatus of claim 1 wherein said mounting means includes means formed integral with the central portion of said flexible valve member for mounting the valve member on said container with the periphery of said valve member engaging the container around said opening.

* * * * *